United States Patent [19]

Laipply

[11] 4,378,333

[45] Mar. 29, 1983

[54] DEVICE FOR PREPARING BLOOD SMEARS ON GLASS SLIDES AND METHOD THEREFOR

[76] Inventor: Thomas C. Laipply, 7946 Mulberry Rd., Chesterland, Ohio 44026

[21] Appl. No.: 215,237

[22] Filed: Dec. 11, 1980

[51] Int. Cl.³ .............................................. B01L 3/02
[52] U.S. Cl. ................................ 422/100; 73/864.11; 73/864.72; 128/760; 128/762; 128/767; 210/927; 422/101; 435/30; 435/292
[58] Field of Search ............. 422/100, 101; 23/230 B; 73/864.02, 864.11, 864.72, 864.91; 128/765, 763, 770, 771, 760, 767, 762; 435/30, 292, 294, 287, 765; 210/927

[56] References Cited

U.S. PATENT DOCUMENTS

| | | | |
|---|---|---|---|
| 2,376,231 | 5/1945 | Cohn | 73/864.01 |
| 2,423,173 | 7/1947 | Brady et al. | 73/864.02 |
| 2,595,493 | 5/1952 | Slaby et al. | 73/864.11 |
| 3,045,494 | 7/1962 | Gerade | 128/765 |
| 3,505,858 | 4/1970 | Kohn | 73/864.02 |
| 3,640,268 | 2/1972 | Davis | 128/759 |
| 3,718,133 | 2/1973 | Perry et al. | 73/864.11 |
| 3,748,909 | 7/1973 | Koo | 73/864.11 |
| 3,864,979 | 2/1975 | Ayres | 422/100 |
| 4,003,262 | 1/1977 | Gerarde et al. | 128/763 |
| 4,054,061 | 10/1977 | Valt | 73/864.11 |
| 4,116,637 | 9/1978 | Kitahara | 422/100 |

OTHER PUBLICATIONS

"Gelman Electrophoresis Chambers"—Electrophoresis, p. 294.
"Olympus Hite Electrophoresis System Automated Serum Protein Profiling"—Olympus Corporation of America.
"Now Showing, 'Automated Electrophoresis'"—Olympus Corporation of America.
"The Fully Mechanised Serum-Protein-Elektrophoresis with the Olympus-Hite-System" by Dr. Jurgen Fuhr.
"General Electrophoresis Equipment Applicators".
"Unopette Test 5855, WBC/Platelet Determination for Manual Methods"—8/77, P80155(CC), cols. 1–8.
"Unopette Test 5857, Cyanmethemoglobin Determination for Manual Methods," cols. 1–5.

*Primary Examiner*—William F. Smith
*Attorney, Agent, or Firm*—Maky, Renner, Otto & Boisselle

[57] ABSTRACT

An integral device for preparing a smear of blood or other sample on a glass slide or other surface is disclosed. The device includes as an operatively integral structure an elongate reservoir having a tip at one end for drawing blood into the reservoir, for example by capillary action or aspiration, and delivering controlled quantities of blood from the reservoir to a slide. Attached to the opposite end of the reservoir a smearing device has an edge cooperable with the surface of the slide to smear blood deposited by the tip. Using the device, a person would manually hold the same in position to draw blood via the tip into the reservoir, would then manipulate the device to deposit a quantity of blood onto the surface of a slide, and while still holding the device would turn the same to place the smearing edge in contact with the slide and would effect relative movement therebetween to smear the blood.

19 Claims, 12 Drawing Figures

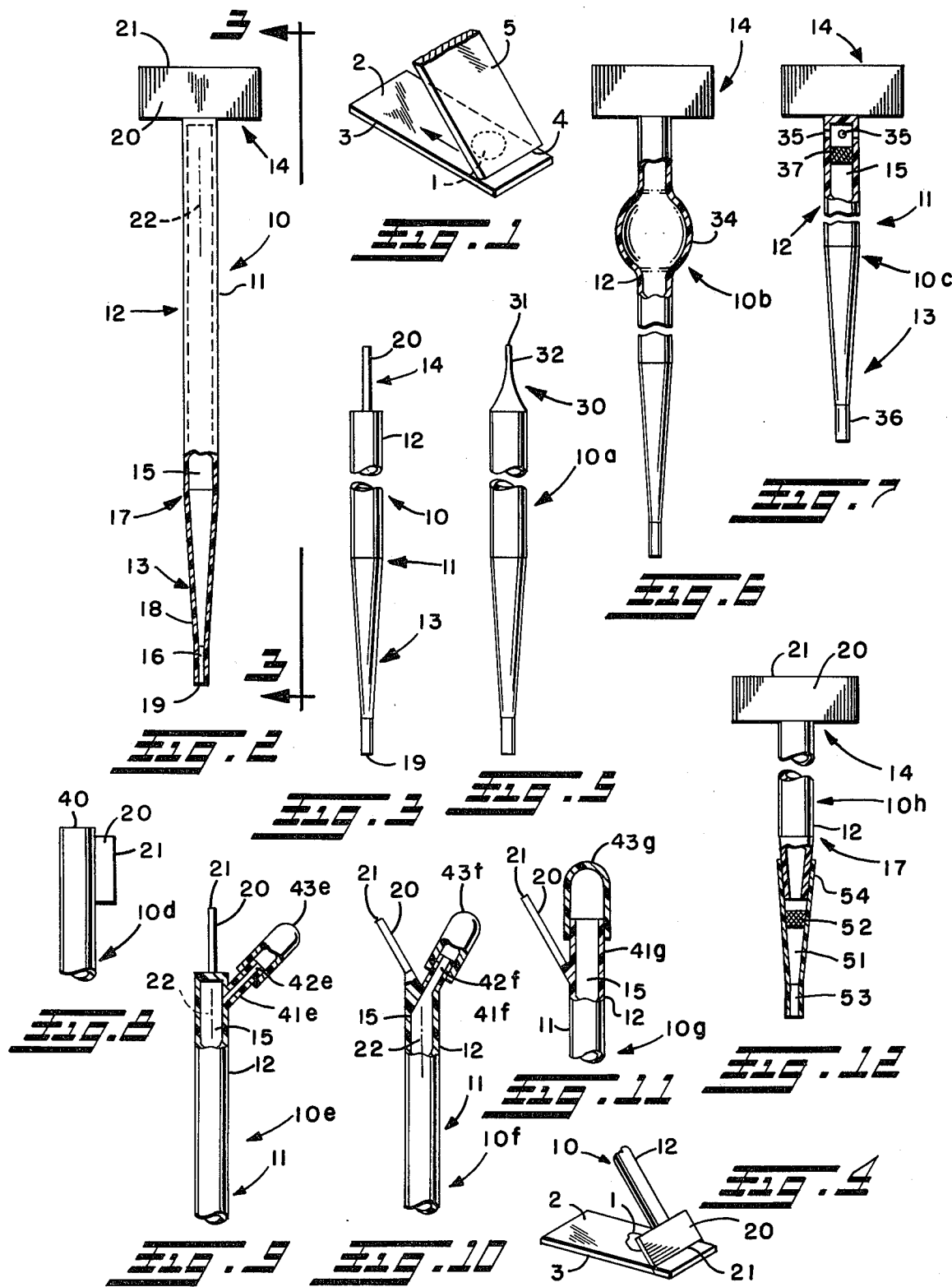

DEVICE FOR PREPARING BLOOD SMEARS ON GLASS SLIDES AND METHOD THEREFOR

TECHNICAL FIELD

The present invention relates generally, as indicated, to preparation of thin smears of a sample on a surface and, more particularly, to the preparation of peripheral blood smears on glass slides.

The traditional method of making a thin smear of a sample, such as blood, on a glass slide, or on another surface, for staining and/or microscopic examination involves several steps usually carried out with plural elements. The more elements involved and the more steps and manipulations required, the greater will be the cost of labor and the chance of contamination of the sample and physical contact with the sample by a technician.

Referring to blood sample analysis, for example, the first step according to the mentioned traditional method often is the mixing of a patient's blood sample contained in a covered test tube or the like by inverting that tube several times. Then an aliquot of blood is aspirated from the test tube by passive flow into a capillary tube; frequently the test tube must be held in tilted orientation by one hand of the technician while the other hand inserts a capillary tube into the sample. A small amount of blood is deposited on the surface of a glass slide by touching the capillary tube to the slide surface; sometimes several touchings are required to obtain a deposit of adequate size. Then the capillary tube is laid down or discarded. Finally, a further glass slide is grasped, positioned at an angle along the original slide surface, and moved along that surface dragging the blood behind it by surface tension thus forming the desired thin smear.

There are a number of disadvantages attendant the traditional method summarized above. For example, both hands of a technician usually are used to perform the several steps; this increases the possibility of sample contamination and/or contact of the sample with the technician and further increases the amount of skill required to carry out the steps and the price for the same. Moreover, the need to take up and to set down or to discard the various paraphernalia required to perform the traditional method of making blood smears increases the time required therefor and the commensurate costs and further increases the possiblity of contamination or contact as was mentioned earlier.

Using the traditional method to prepare blood smears some difficulty in controlling the quantity of blood deposited by the capillary tube on the glass slide has been experienced. Typically the quantity of blood so deposited is a function of how hard and the number of times the capillary tube is tapped against the glass slide, a relatively imprecise technique. The capillary tubes are sometimes heparinized to facilitate outflow of blood therefrom. Also, when more than one slide is to be prepared from the blood contained in a test tube, it frequently is the case that several fillings of one or more capillary tubes are required to obtain adequate blood therein for deposit on the plural slides.

The applicant has discovered a new device for making smears of a sample on a surface and a method for making such smears that overcome a number of the above-mentioned and/or other disadvantages previously encountered in the traditional method. The invention, in accordance with the best mode and preferred embodiment will be described hereinafter with reference to a device for preparing a smear of a blood sample on a glass slide; however, it will be appreciated that the various features of the invention may be applicable to the preparation of smears of a sample other than blood on a surface other than a glass slide, and these are intended to be within the spirit and scope of the present invention.

SUMMARY OF THE INVENTION

Briefly, the invention is an operatively integral device that provides plural functions that previously were carried out by multiple discrete components. Operatively integral means that although parts of the device may be separable, for use all of the parts are assembled in a unified device as will become clearer from the following description. The device permits steps to be carried out in a more efficient manner and with minimum possibility of contamination of the sample and possibility of sample contact with the technician than was heretofore possible. The device includes a body, preferably of elongate form having a hollow interior that provides a reservoir for a sample drawn therein, a passage at one end of the reservoir through which sample may be drawn and discharged under the incentive or influence, for example, of capillary action or aspiration, and at or near the other end of the hollow body a smearing edge or surface for smearing a sample deposited onto a surface while the overall device is partly or wholly inverted to avoid inadvertent discharge of sample from the passage. The smearing end has an edge or a surface preferably contoured to fit in intimate engagement with the surface on which the sample is to be smeared to obtain uniformity in the smear. Preferably a fairly substantial amount of sample may be contained in the reservoir to enable discharge thereof to make smears on plural slides or the like and there is provided means for relatively accurately controlling the quantity of sample deposited on surfaces via the passage.

Moreover, a separate tip, which may be of the disposable or reusable type, may be operatively connected to the hollow body of the device; preferably the tip itself provides the reservoir function. Isolation of the sample from the hollow body of the device prevents contamination of the sample in the tip reservoir while the device itself provides the incentive to draw sample into the tip reservoir. The main body and the easily cleaned smearing end of the device, then, may be reused with plural tips that themselves provide contaminant-free environment for the samples drawn therein.

With the foregoing in mind, in accordance with one aspect of the invention a device for preparing sample smears on a surface includes as an operatively integral structure a drawing means for drawing a quantity of sample from a supply thereof and for depositing a controlled quantity of such drawn sample onto a surface for smearing thereon and a smearing means for smearing or spreading such deposited controlled quantity of sample on such surface.

According to another aspect, a device for making a sample smear on a surface with minimum sample contamination includes an integral assembly having a reservoir for containing a sample, a passage for passing a sample into the reservoir and for discharging a quantity of sample from the reservoir onto a surface, and smear means for smearing the sample on the surface.

According to an additional aspect, a device for making a smear of a sample on a surface includes first and second portions and an intermediate portion connected therebetween, at least one of the first and intermediate portions including a reservoir for containing a sample, the first portion including a passage for delivering a sample from a supply thereof into the reservoir and from the reservoir to a surface, and the second portion including a smearing means cooperative with the surface for smearing a sample thereon.

According to a further aspect, a tip for a sample obtaining and delivering device which has a hollow body for mounting the tip and providing incentive to draw sample into the tip, includes a tip body, a reservoir in the body for containing a sample, a relatively small cross-section inlet at one end of the tip body for passing sample in and out of the reservoir, a coupling means for coupling the tip body to the hollow body, and a means for effecting at least a partial fluidic coupling between the hollow portion of the hollow body and the reservoir.

According to even another aspect of the invention, a method of making a sample smear on a surface using an integral device, includes drawing a quantity of a sample material into the device from a supply of the sample, delivering a quantity of the sample from the device onto the surface, and moving at least a portion of the device over at least a portion of the surface to smear the sample thereon.

With the foregoing in mind, a primary object of the invention is to facilitate the making of a smear of a sample on a surface and, more particularly, to make a smear of a blood sample on the surface of a glass slide.

Other objects are to minimize the time and cost for making sample smears, especially blood smears on slides.

Additional objects are to minimize the possibility of contaminating a sample smear, especially a blood smear on a slide, and to minimize the possibility of contact of the sample with a technician making a sample smear.

A further object is to improve the control of the quantity of sample deposited on a surface on which a smear is to be made, especially a blood sample.

Still other objects include facilitating mixing a sample in a test tube or the like intended for making a smear and to expedite the making of plural smears on respective surfaces.

Still an additional object is to provide an integral device for preparing blood smears on glass slides improved in the noted respects.

Still a further object is to provide an improved method for making blood smears or the like.

These and other objects and advantages of the present invention will become more apparent as the following description proceeds.

To the accomplishment of the foregoing and related ends, the invention, then, comprises the features hereinafter fully described in the specification and particularly pointed out in the claims, the following description and the annexed drawing setting forth in detail certain illustrative embodiments of the invention, these being indicative, however, of but several of the various ways in which the principles of the invention may be employed.

BRIEF DESCRIPTION OF DRAWING

In the annexed drawing:

FIG. 1 depicts the traditional method of making a thin peripheral blood smear on a glass slide;

FIG. 2 is a front elevation view, partly broken away in section, of a device for preparing blood smears on glass slides in accordance with the present invention;

FIG. 3 is a side elevation view of the device of FIG. 2 looking generally in the direction of the arrows 3—3 thereof;

FIG. 4 is a schematic illustration depicting use of the device of FIGS. 2 and 3;

FIG. 5 is a side elevation view of a modified device having a wedge-shape smearing means;

FIG. 6 is a front elevation view, partly broken away in section, of a modified device having an enlarged stem or body segment;

FIG. 7 is a front elevation view, partly broken away in section, of a modified device having ports for admission of air into the reservoir and a semi-porous plug in the reservoir;

FIG. 8 is a front elevation view of a modified device having a side-mounted smearing means;

FIGS. 9, 10 and 11 are partial side views of modified devices with squeeze bulbs for aspiration incentive; and FIG. 12 is a front view, partly in section, of a modified device with a removable tip having its own internal reservoir.

In the accompanying drawing, like reference numerals are used to designate like parts in the several figures.

Referring initially to FIG. 1, the traditional or prior art method of making a thin smear of blood on a glass slide is depicted. Accordingly, a quantity of blood 1 already has been deposited on the surface 2 of a glass slide 3, for example by tapping a capillary tube (not shown) containing blood to such surface. The edge 4 of a further glass slide 5 then is placed in contact with the surface 2 and is slid therealong to draw the blood sample 1 out along that surface to form the thin smear. It is important that the edge 4 conform in configuration to the surface 2 and to that end the edge 4 is linear for relatively intimate engagement with the flat surface 2. After the smear has been made, the slide 5 ordinarily would be discarded and the smear itself may be used in conventional manner, for example, for analysis purposes.

DETAILED DESCRIPTION OF INVENTION

Turning now more particularly to FIGS. 2, 3 and 4, a device for preparing blood smears on glass slides in accordance with the preferred embodiment and best mode of the present invention is generally indicated at 10. The device 10 preferably is formed of an integral body 11, for example of a plastic material, that may be manufactured, for example, by molding or other technique. The body 11 includes an intermediate portion 12 connected between an inlet/outlet end portion 13 and a smearing end portion 14. The intermediate portion 12 not only interconnects the end portions 13, 14, but also provides a common handle function by which the device 10 may be grasped manually and manipulated for use to draw in a sample, to discharge a sample, and to smear a sample.

More specifically, the body 11 preferably has a hollow interior 15 that provides a reservoir function to contain sample drawn therein. Such sample may be drawn into the reservoir 15 via a narrow, cylindrical, tubular flow passage 16 in the inlet/outlet end portion 13, for example from a test tube or other container holding a supply of blood. The inlet/outlet end 13 is tapered down from the wider area of the preferred cylindrical tubular intermediate body portion 12 and hollow interior 15 thereof commencing approximately at the area designated 17 to the flow passage 16. The gradual taper shown at 18 of truncated conical shape of the inlet/outlet end 13 is preferred to avoid sharp corners, edges or surfaces at which uniform flow may be impeded, blood coagulation may be facilitated, etc. The narrow flow passage 16 facilitates relatively accurate control of the quantity of sample delivered from the terminal end 19 thereof onto a slide.

As is illustrated in FIGS. 2, 3 and 4, the reservoir 15 is closed at the smearing end portion 14 to prevent spillage of fluid from the latter when the device 10 is inverted for use to smear blood on a slide. At the smearing end is a smearing piece 20 of rectangular plan and cross-section. The smearing piece 20 is attached to the body 11, for example by molding integrally with the latter. The edge 21 of the smearing piece 20 is about the same size and shape as the edge 4 of the glass slide 5 (FIG. 1) or is of any other desired shape suitable for mating with the surface, such as surface 2 of the slide 3 (FIG. 1) on which a smear is to be made. Thus, in the illustrated example in FIGS. 2–4, the edge 21 is substantially linear to mate with a planar surface. The cross-section shape of the smearing piece 20 may be, for example, rectangular, trapezoidal, square, rhomboidal, angulated, polygonal, wedge-shape, or any other shape that permits the desired smearing of fluid along a surface.

The material of which the body 11 is made preferably has suitable rigidity to maintain the general configuration as illustrated and, additionally, preferably has a capacity for resilient deformation. Accordingly, by squeezing the intermediate portion 12 and releasing the same a vacuum or aspirating effect can be created providing incentive to draw sample into the reservoir 15; similarly, upon squeezing the intermediate portion 12 a controlled quantity of sample may be delivered through the flow passage 16 for deposit onto a slide. The material of which the body 11 is made also preferably is of a type that will be unaffected by the particular sample with which the same ordinarily would be expected to be used. It also will be appreciated that a variety of materials may be used for the body 11, as desired, depending on the required rigidity, flexibility, chemical stability, and so on. For example, as will be described in greater detail below, the body 11 may be formed of plastic, such as polyethylene or polypropylene, or glass with provisions made to effect a drawing of blood into the reservoir 15.

Using a plastic material for the device 10, though, results in a number of advantages over the prior glass slide smearing mechanism (the slide 5 illustrated in FIG. 1) and the prior glass capillary tubes. Specifically, the plastic material of which the smearing piece 20 may be made has a significantly lower surface energy with respect to blood than does a glass slide and, therefore, allows for less carry-over of blood from one slide to the next when making multiple smears with a given smearing piece; this facilitates cleaning the smearing piece 20 too. Moreover, the plastic material of the inlet/outlet end portion 13 with its lower surface energy relative to the glass surface of a conventional capillary tube eliminates the need for a heparinized surface thus resulting in a further cost savings.

The overall length of the device 10 and the diameter of the body 11, particularly the intermediate portion 12 thereof are greater than the smaller dimensions of a conventional capillary tube; therefore, the grasping, manipulation and use of the device 10 are facilitated thereby to facilitate the making of slide smears, especially when using only one hand. The inlet/outlet end portion 13 may be from about 1 to about 4 cm. in length and from about 1 to about 1.3 mm. in internal diameter. The smearing piece may be approximately 2.5 cm. wide along edge 21 (the width of a glass slide), about 0.5 to about 1.0 cm. long, i.e. in the direction approximately parallel to the axis 22 of the device 10, and about 0.1 cm. thick, which is the thickness of a typical glass slide.

In using the device 10 the inlet/outlet end portion 13 may be inserted into a supply of blood contained in a tube while the axis 22 of the device is in a generally vertical or near vertical direction such that the terminal end 18 is lower than the smearing end portion 14. The intermediate portion 12 may be squeezed and released several times to cause mixing of the blood in the test tube supply thereof. After the required mixing has been effected, one further squeeze and release of the intermediate portion 12 will draw a quantity of blood into the reservoir 15. The inlet/outlet end portion 13 then is placed near the surface 2 of a glass slide 3 and the intermediate portion 12 is squeezed a controlled amount to deliver through the flow passage 16 a controlled aliquot of blood 1 onto the surface 2 of the slide. Preferably the capacity of the reservoir 15 is adequate to deposit several controlled aliquots of blood onto respective slides. The device 10 then is turned over or inverted to orient the inlet/outlet end portion 13 higher than the smearing end portion 14, as is shown, for example, in FIG. 4 to enable use of the smearing edge 21. More particularly, the edge 21 is placed in engagement with the surface 2 of the slide 3 and is moved therealong to draw blood along the slide to make the smear. With the device 10 so inverted during the smearing step, the outlet 23 of the flow passage 16 will be pointed in a generally upward direction in order to avoid inadvertent discharge of blood from the reservoir 15.

It will be appreciated that by following the just-described method, there is no need to pick up the test tube supply of blood to mix the same, for the device 10 may be used to effect mixing. There is no need to pick up and to discard a capillary tube or a separate glass slide, for the device 10 while being held only in a single hand of a laboratory technician may be used not only to effect the aforesaid mixing but also to draw in a sample, to deposit a sample, and to effect smearing of the sample on the slide. When multiple smears are made with the device 10, excess blood may be wiped off the smear piece 20, if desired, between slides.

The several modified embodiments illustrated in FIGS. 5–12 now will be described. It will be appreciated that features shown in the several modified embodiments may be combined or used with each other and/or with those of the preferred embodiment shown in FIGS. 2–4.

In FIG. 5 a modified smear piece 30 having a wedge-shape cross-section has been substituted on the device 10a for the rectangular cross-section smear piece 20 of FIGS. 2–4. The narrower edge 31 relative to the thickness of the edge 21 and the curvature in the surface 32 of the smear piece 30 provide a different feel and control of the smearing as the edge 31 is drawn along a slide 3. The relatively large base area 33 of the smear piece 30 also provides a larger area for increased strength of attachment to the intermediate portion 12 of the device 10a compared to the relatively narrower area of the smear piece 20.

In the device 10b illustrated in FIG. 6 there is an enlarged body segment 34 in the intermediate portion 12 of the body 11. The segment 34 also may be resiliently deformable such that squeezing and release thereof will have minimum deforming effect on the major cylindrical extent of the intermediate portion 12. More accurate control of the total amount of resilient deformation effected and/or increased displacement in the intermediate portion 12, then, could be achieved preferably with a corresponding improvement in accuracy of control of the size of the aliquot delivered to a slide. Additionally, the enlarged segment 34 may provide increased reservoir capacity inside the body 11 of the device 10b.

In FIG. 7 the device 10c has ports 35 in the intermediate portion 12 near the smearing end portion 14. The ports 35 provide communication between the reservoir 15 and the external environment of the device 10c whereby the incentive for blood to be drawn into the reservoir through the inlet/outlet end portion 13 may be by capillary action. Accordingly, the diameter and length of the flow passage in the remote tip 36 of the inlet/outlet end portion 13 preferably is such that the desired capillary action will be effected. Therefore, the drawing of a sample into the device 10c may be with minimum disturbance to the blood in the supply thereof. The body 11 of the device 10c may be of relatively rigid, usually nondeformable material, such as glass, since there ordinarily would not be a need to deform the same to draw sample therein. Discharge of the sample from the reservoir 15 onto a slide may be effected by tapping the end 23 to the slide surface. Alternatively, the intermediate portion 12 of the body 11 may be resiliently deformable in order to utilize that property for discharging blood onto a slide. To prevent blood from the reservoir 15 reaching the ports 35 and leaking therefrom or blocking the same, a plug 37 is placed in the reservoir. The plug 37 preferably is absorbent of liquid that would engage the same an amount suitable to block at least briefly passage of the liquid through to the ports 35. On the other hand, the material of which the plug 37 is made preferably is porous to air to allow passage of the same to obtain the desired capillary action for flow by surface tension.

In the device 10d illustrated in FIG. 8 the smearing piece 20 is mounted on the side of the intermediate portion 12 rather than at the end 40 thereof. In this embodiment the device 10d need only be inverted approximately 90° from vertical for use of the smearing edge 21 to smear blood on a slide. During such smearing step, then, there would be a reduction in the pressure head of the blood in the reservoir over the other embodiments.

In FIGS. 9-11 the body 11 of the devices 10e, 10f, 10g preferably are of relatively rigid material not intended to be resiliently deformed. In the device 10e an extension 41e leads from the intermediate portion 12 at an acute angle relative to the smearing piece 20, which is positioned in a plane approximately parallel to the axis 22. The extension 41e has a passage 42e therein coupling with the reservoir 15 at one end and at the other end being covered by a squeeze bulb 43e. The bulb 43e may be squeezed to aspirate blood into the reservoir 15. The remaining portion of the body 11 of the device 10e, as is also the case in the devices 10f and 10g, may be the same as the device 10 described above.

The devices 10f, 10g illustrated in FIGS. 10 and 11 are similar to the device 10e with the exception of the angle at which the extensions 41f, 41g connect with the intermediate portion 12 of respective bodies 11 and the angle at which the smearing pieces 20 connect with the intermediate portion 12. In the device 10f the extension 41f is located at the end of the intermediate portion 12, and the smearing piece 20 also is positioned at an acute angle relative to the axis 22 to facilitate spacing or separating of the smearing piece 20 and the squeeze bulb 43f. Such separation helps to avoid contamination of the edge 21 when the laboratory technician holds the bulb 43f to squeeze the same. In the device 10g the extension 41g simply is a linear continuity of the intermediate portion 12. The smearing piece 20 of the device 10g is mounted at an angle with respect to the axis 22 in order to isolate the edge 21 from the squeeze bulb for the purpose described with reference to the device 10f.

Turning briefly to FIG. 12, there is illustrated a tip 50, which may be used with any of the devices 10 described above, especially with their respective inlet/outlet end portions 13 being so modified as to couple well with the tip 50. It is intended that the tip 50 be a throw-away item or alternatively be capable of cleaning and/or sterilization separately from the device 10h. It also is intended that the tip 50 have its own internal reservoir 51 with a plug 52, similar to the plug 37 mentioned above, to prevent blood in the reservoir 51 from entering the hollow interior or from contacting any portion of the body 11 of the device 10h. The tip 50 has a narrow diameter generally cylindrical end 53 through which blood may pass to enter and to leave the reservoir chamber 51. Preferably there is a tight fit connection 54, for example provided by interfacing truncated conical sections or other conventional means to connect the tip 50 to the body 11 of the device 10h. Moreover, preferably at least a portion of the body 10h is hollow and is fluidically coupled with the hollow interior of the tip 50 so that drawing of blood into the reservoir 51 of the tip may be effected by the aspirating or capillary functions described above with reference to FIGS. 2-11. It will be appreciated that separate tips 50 may be used for making smears from blood taken from different respective supplies, although the same body 11 may be used for making each of those smears. The smearing piece 20 of the device 10h, in that event, could be easily cleaned with a sterilizing solution between respective smears from different supplies.

STATEMENT OF INDUSTRIAL APPLICATION

With the foregoing in mind, it will be appreciated that the device 10 in accordance with the present invention may be utilized to facilitate the making of blood smears and the like.

I claim:

1. A device for preparing sample smears on a flat surface comprising as an operatively integral structure drawing means for drawing a quantity of sample from a supply thereof and for depositing a controlled quantity of such sample onto such surface for smearing thereon, an elongate tubular body having a hollow interior, said drawing means comprising means for drawing sample into said hollow interior, inlet/outlet means at one end of said tubular body for passing sample into and out from said hollow interior, smearing means for spreading on such surface such deposited controlled quantity of sample, said smearing means comprising a relatively rigid smearing body and a continuous linear edge configured to conform to such surface for intimate engagement therewith to spread such sample on such surface in a substantially uniform manner, and said smearing means being attached to the end of said tubular body opposite the end at which said inlet/outlet means is located and separate from said drawing means.

2. The device of claim 1, such surface comprising the surface of a glass slide, such sample comprising blood, and said linear edge having a length approximately equal to the width of such slide.

3. The device of claim 1, said smearing body comprising a wedge-shape member having a linear edge for smearing.

4. The device of claim 1, said tubular body comprising a handle for manually holding the device to use the same for drawing and depositing sample and for smearing a sample.

5. The device of claim 1, said tubular body including an enlarged segment therein.

6. The device of claim 1, further comprising inlet/outlet means at an end of said tubular body for passing fluid drawn and deposited by the device.

7. The device of claim 6, said inlet/outlet means comprising a tapered end portion with a relatively narrow inner diameter cylindrical flow passage having a terminal end insertable into a supply of sample.

8. The device of claim 6, said inlet/outlet end comprising a constant inner diameter flow passage portion including a terminal end insertable into a sample for drawing in the same.

9. The device of claim 8, said flow passage portion and said hollow interior of said tubular body being fluidically coupled and further comprising port means for equalizing pressure inside said hollow interior with ambient pressure outside said tubular body.

10. The device of claim 9, further comprising means for at least partly blocking flow of liquid sample in said hollow interior from said port means while permitting air pressure communication between all portions of said hollow interior and said port means.

11. The device of claim 1, said elongate tubular body having an axis, said smearing means being mounted on said tubular body in a direction parallel to said axis, said linear edge being relatively fixed to extend in a direction substantially transverse to the direction of said axis.

12. The device of claim 11, said smearing body comprising a smearing surface means for holding said smearing edge at a location spaced apart from such axis, and further comprising means for coupling said smearing surface means at one end to said tubular body to extend at an acute angle away from such axis.

13. The device of claims 1 or 12, said drawing means comprising a squeeze bulb means.

14. The device of claim 1, said smearing means being mounted on the side of said tubular body.

15. The device of claim 1, said body comprising relatively rigid material having a resilient deformable characteristic.

16. The device of claim 15, said tubular body and said smearing body comprising plastic.

17. The device of claims 1 or 11, wherein the device comprises a rigid material such as glass.

18. The device of claim 1, further comprising a tip removably mounted at said inlet/outlet means, said tip comprising a tip body, reservoir means in said tip body for containing a sample, a relatively small cross-section inlet means at one end of said tip body for passing sample in and out of said reservoir means, and means for effecting at least a partial fluidic coupling between the hollow portion of such body and said reservoir means.

19. The device of claim 18, said tubular body having port means therein for equalizing pressure inside the same and inside said reservoir means with the ambient pressure outside the device and outside said tip.

* * * * *